United States Patent [19]

Wermuth et al.

[11] Patent Number: 4,983,603
[45] Date of Patent: Jan. 8, 1991

[54] TRICYCLIC CHOLINERGIC RECEPTOR AGONISTS

[75] Inventors: Camille G. Wermuth, Strasbourg; Paul Worms, Gely du Fesc; Jean-Jacques Bourguignon, Hipsheim; Roger Brodin, Montpellier, all of France

[73] Assignee: Societe Anonyme: SANOFI, Paris, France

[21] Appl. No.: 288,861

[22] Filed: Dec. 23, 1988

[30] Foreign Application Priority Data

Dec. 24, 1987 [FR] France .................. 87 18187

[51] Int. Cl.$^5$ .................. C07D 495/04; C07D 491/05; A61K 31/535; A61K 31/50
[52] U.S. Cl. .................. 514/232.8; 514/248; 544/115; 544/234; 549/23; 549/401
[58] Field of Search ............ 544/234, 115; 514/248, 514/232.8

[56] References Cited

U.S. PATENT DOCUMENTS 3,464,988 9/1969 Holava et al. .................. 544/234
4,701,453 10/1987 Sircar et al. .................. 544/234
4,910,199 3/1990 Bourguignon et al. .......... 544/117

FOREIGN PATENT DOCUMENTS 2141697 1/1973 France .

OTHER PUBLICATIONS

Chapman et al., In "Alzheimer's and Parkinson's Diseases", p. 329 (1986).
McKhann et al., *Neurology,* 34 p. 939 (1984).
Fisher et al., *Proc. Int. Symp. Muscarinic Cholinergic Mechanisms,* p. 132 (1986).
Palacios et al., *Eur. J. Pharmacol.,* 125 p. 45 (1986).
Tariot et al., *Arch. Gen Psychiatry* 45, p. 901 (1988).
Wettstein et al., *Psychopharmacology,* 84, p. 572 (1984).
Harbaugh et al., *Neurosurgery,* 15, p. 514 (1984).
Hollander et al., *Brit. Med. Bull.,* 42, p. 97 (1986).
*Science News,* vol. 136, No. 5, p. 68 (Jul. 29, 1989).

Nigel J. M., Birdsall et al, ISI Atlas of Sciences Pharmacology/1987, pp. 98–100.

*Primary Examiner*—Mukund I. Shah
*Assistant Examiner*—E. Bernhardt
*Attorney, Agent, or Firm*—Foley & Lardner, Schwartz, Jeffery, Schwaab, Mack, Blumenthal & Evans

[57] ABSTRACT

The invention relates to novel tricyclic derivatives which are agonists of cholinergic receptors.

These derivatives have the formula

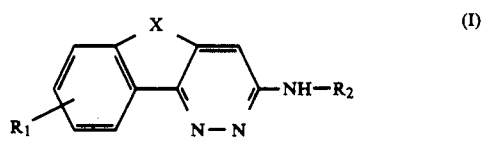

(I)

in which $X = O$, $S$, $-OCH_2-$ or $-SCH_2-$; $R_1 = H$ or halogen; and $R_2 =$

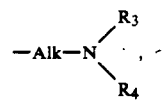

in which Alk is an alkylene group and $R_3$, an $R_4$, which are identical or different, are hydrogen or a lower alkyl group, or $R_3$ and $R_4$, with the nitrogen atom to which they are bonded, form a 5- or 6-membered cyclic amino group optionally containing a second heteroatom; or $R_2$ is a group

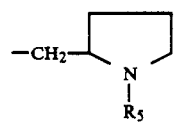

where $R_5 = C_1-C_4$-alkyl.

Application: agonists of cholinergic receptors.

4 Claims, No Drawings

TRICYCLIC CHOLINERGIC RECEPTOR AGONISTS

Senile dementia and in particular dementia of the Alzheimer type are serious complaints whose frequency is tending to increase with the increasing longevity of the population.

The studies undertaken by various authors have demonstrated, in Alzheimer's disease, the existence of a specific deficit of cortical cholinergic markers, causing serious disorders of the higher functions.

The results obtained using muscarinic agonists to treat senile dementia have proved encouraging. However, there are only a small number of muscarinic agonists in existence and they have been found difficult to manage in man.

Consequently, it is totally desirable at the present time to search for post-synaptic muscarinic agonists as a treatment for Alzheimer's disease.

The advantage of having selective central muscarinic agonists for correcting the cholinergic deficit in Alzheimer's disease has been mentioned especially in ISI Atlas of Science: Pharmacology (1987), p. 98 to 100.

It is to this problem that the present invention attempts to bring a solution in the form of novel products which act selectively on the $M_1$ central muscarinic receptors.

According to a first feature, the present invention relates to novel tricyclic compounds having the general formula

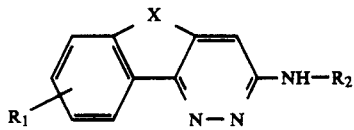

in which:

X represents an oxygen or sulfur atom or X represents a group —OCH$_2$— or a group —SCH$_2$—;

R$_1$ represents hydrogen or a halogen atom, preferably chlorine; and

R$_2$ represents:

a group

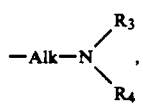

in which:

Alk represents a linear or branched alkylene group having from 2 to 5 carbon atoms, and R$_3$ and R$_4$ each independently represent hydrogen or a lower alkyl group having 1 to 4 carbon atoms, or R$_3$ and R$_4$, with the nitrogen atom to which they are bonded, form a 5- or 6-membered cyclic amino group optionally containing a second heteroatom, and especially the pyrrolidin-1-yl, piperidino, morpholino or piperazin-1-yl groups; or a group

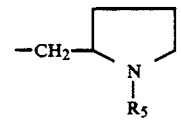

in which R$_5$ represents a lower alkyl group having 1 to 4 carbon atoms, and to their addition salts with pharmaceutically acceptable mineral or organic acids.

According to a second feature, the invention relates to a process for the preparation of the compounds of formula (I), which can be represented by the following scheme:

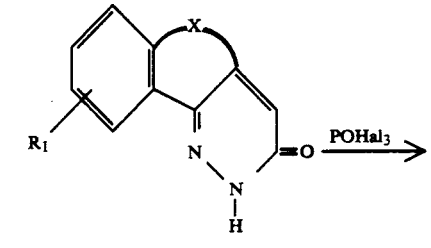

R$_6$ = H or C$_2$H$_5$

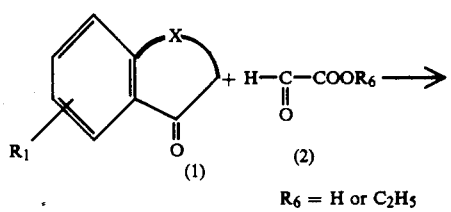

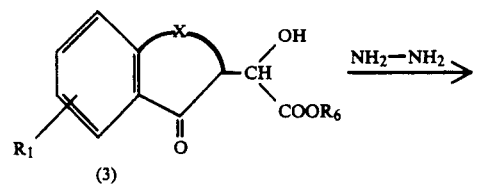

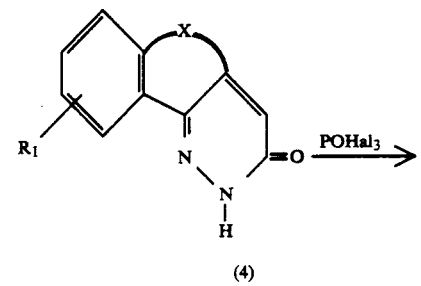

Hal = Cl, Br $$H_2N-R_2 \longrightarrow (I)$$
(6)

Reaction of ethyl glyoxylate or glyoxylic acid (2) with a ketoheterocycle (1) at a temperature of between 60° and 150° C. gives the hydroxyester or hydroxy-acid (3). This usually contains a small amount of the corresponding dehydration product (acrylic ester). It can be purified by chromatography or the crude product can be used direct for the next step.

The product (3) yields the pyridazone (4) on heating with hydrazine hydrate. The reaction is carried out either with a large excess of hydrazine hydrate or in a solvent selected from the group comprising hydroxylated solvents, especially n-butanol or ethanol.

When treated under reflux with an excess of phosphorus oxychloride or oxybromide, the pyridazone (4) yields the halogen derivative (5).

Finally, the compound (I) is obtained by heating the halogen derivative (5) with the derivative (6) in a suitable solvent.

The solvent can be either a hydroxylated solvent, such as n-butanol, or dimethylformamide, or it can consist of an excess of the derivative (6).

If the substitution reaction of the chlorine derivative is found to be slow, it can be facilitated by the addition of a reaction activator, for example ammonium chloride.

If desired, the resulting compounds (I) can be converted to salts by a known process.

The starting materials of formula (1) are known or can be prepared by known processes.

The following Examples are given in order to illustrate the invention.

EXAMPLE 1

2-(2-Morpholinoethylamino)-9,10-dihydro-9-oxa-3,4-diazaphenanthrene dihydrochloride (SR 96094 A)

(I) $X = -O-CH_2-$; $R_1 = H$; $R_2 =$

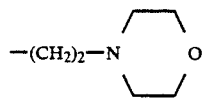

(a) Ethyl (4-oxochroman-3-yl)glycolate

A mixture of 14 g of chroman-4-one and 14.5 g of ethyl glyoxylate is heated for 9 hours at 135° C.

It is chromatographed on a silica column and the expected product (3.6 g) is isolated in the form of yellow crystals on elution with a hexane/ethyl acetate mixture (80/20 vol/vol). M.p.=50° C.

(b) 2-Oxo-2,3,9,10-tetrahydro-9-oxa-3,4-diazaphenanthrene 2.78 ml of hydrazine hydrate are added to a solution of 13 g of the ester prepared under (a) in 150 ml of n-butanol and the mixture is stirred for 3 hours at room temperature and then refluxed for 24 hours.

The crystals formed on cooling are filtered off (3.45 g). M.p.=>250° C.

1.4 ml of hydrazine hydrate are added to the filtrate and the mixture is refluxed for 24 hours.

2.45 g of the same product are obtained on cooling.

(c) 2-Chloro-9,10-dihydro-9-oxa-3,4-diazaphenanthrene 5 g of the product prepared above and 75 ml of phosphorus oxychloride are heated at 80° C. for 1 hour.

The reaction mixture is poured dropwise into an ice/water mixture and then rendered alkaline with sodium hydroxide (33% solution).

The precipitate is filtered off, washed copiously with water and then dried under vacuum.

The solid is recrystallized from absolute ethanol.

4.75 g of the expected product are obtained. M.p.=208° C.

(d) SR 96094 A

A mixture of 4.37 g of the chlorine derivative prepared above, 13.1 ml of 2-morpholinoethylamine and 2.13 g of ammonium chloride is heated at 120° C. for 2 hours.

The reaction mixture is poured into water and extraction is carried out with ethyl acetate. The organic phase is extracted with a dilute solution of hydrochloric acid and the aqueous phase is separated off. It is rendered alkaline with potassium carbonate and extracted with ethyl acetate. The solution is washed with water, dried over sodium sulfate and evaporated to dryness. The solid is purified by chromatography on a silica column. 2 g of the expected product are obtained on elution with an ethyl acetate/methanol/aqueous ammonia mixture (80/10/10 vol/vol). M.p.=149° C.

Dihydrochloride 1 g of the base obtained above is dissolved in isopropanol and 0.55 ml of a concentrated solution of hydrochloric acid is added. The mixture is evaporated to dryness and the residue is crystallized from absolute ethanol to give a yellow solid (0.9 g). M.p.=216° C.

The dihydrochloride crystallizes with 2 molecules of water.

EXAMPLE 2

2-(2-Diethylaminoethylamino)-9,10-dihydro-9-thia-3,4-diazaphenanthrene dihydrochloride (SR 96056 A)

(I) $X = -S-CH_2-$; $R_1 = H$; $R_2 =$

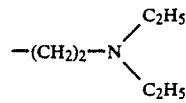

The procedure is the same as in Example 1, thiochroman-4-one being used instead of chroman-4-one as the starting material.

The following are obtained successively in the same manner:

(a) Ethyl (4-oxothiochroman-3-yl)glycolate in the form of an oil. Yield=62%.

(b) 2-Oxo-2,3,9,10-tetrahydro-9-thia-3,4-diazaphenanthrene. M.p.=>250° C. Yield=32%.

(c) 2-Chloro-9,10-dihydro-9-thia-3,4-diazaphenanthrene. M.p.=190° C. Yield=92%.

(d) SR 96056 A.

Base: M.p.=146° C. after recrystallization from isopropanol.

Dihydrochloride: M.p.=162° C. (isopropanol). Yield=70%.

The dihydrochloride crystallizes with 3 molecules of water.

EXAMPLE 3

2-(2-Morpholinoethylamino)-9-oxa-3,4-diazafluorene dihydrochloride (SR 44288 A)

(I) $X = O$; $R_1 = H$; $R_2 =$

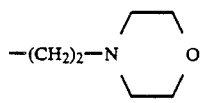

(a) 2-Oxo-2,3-dihydro-9-oxa-3,4-diazafluorene

A mixture of 4 g of 3-oxo-2,3-dihydrobenzofuran and 6.18 g of glyoxylic acid is heated for 4 hours at 80° C.

The reaction mixture is taken up in 60 ml of absolute ethanol, 4.48 g of hydrazine hydrate are added and the resulting mixture is refluxed for 65 hours. It is evaporated to dryness under vacuum in a water bath.

The residue is dissolved in ethyl acetate and the solution is then filtered on a silica column using the same solvent as the eluent.

The filtrate is chromatographed twice on a column of silica gel using a 95/5 vol/vol chloroform/methanol mixture as the first eluent and a 90/10 vol/vol chloroform/methanol mixture as the second eluent. 1.2 g of the expected product are finally obtained. M.p.=>260° C.

(b) 2-Chloro-9-oxa-3,4-diazafluorene

A mixture of 1.2 g of the product prepared under (a) and 30 ml of phosphorus oxychloride is heated at 90° C. for 5 hours.

The excess phosphorus oxychloride is evaporated off under vacuum in a water bath and the residue is taken up in iced water. Extraction is carried out with ethyl acetate, the organic solvent is washed with water and dried over sodium sulfate and the solvent is evaporated off under vacuum.

The residue is chromatographed on a column of silica gel.

The expected product (0.8 g) is obtained on elution with ethyl acetate. M.p.=122° C.

(c) SR 44288 A

A mixture of 0.7 g of the chlorine derivative obtained above and 1.34 g of 2-morpholinoethylamine in 50 ml of n-butanol is refluxed for 140 hours.

It is treated as indicated in Example 1 (d) and, after chromatography on silica (eluent: 90/10 chloroform/methanol), 0.4 g of the expected product is obtained.

Dihydrochloride 0.4 g of the base is dissolved in 5 ml of absolute ethanol, 0.34 ml of concentrated hydrochloric acid is then added and the product is left to crystallize.

The crystals are filtered off, washed with a small amount of ethanol and dried under vacuum. Weight=0.3 g. M.p.=>260° C.

The dihydrochloride crystallizes with 1 molecule of water.

EXAMPLES 4 TO 6

By following the same procedure as in Example 3 (c), starting from the chlorine derivative obtained in Example 3 (b) but varying the amine used, the products (I) collated in Table 1 are obtained in the same manner.

TABLE 1

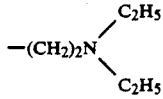

| Example no. | Code no. | $R_2$ | Salt isolated [melting point °C. (solvent)] |
|---|---|---|---|
| 4 | SR 45040 A | $-(CH_2)_2N(C_2H_5)_2$ | Difumarate M.p. = 142–144 (ethanol) |
| 5 | SR 45041 A | $-(CH_2)_3N(C_2H_5)_2$ | Difumarate M.p. = 153–155 (ethanol) |
| 6 | SR 45042 A | $-CH_2-$(1-ethylpyrrolidin-2-yl) | Dihydrochloride (1 molecule of water) M.p. = 204–206 (ethanol) |

EXAMPLE 7

2-(2-Morpholinoethylamino)-9-thia-3,4-diazafluorene dihydrochloride (SR 44289 A)

(I) X=S; $R_1$=H; $R_2$=

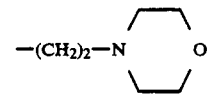

The procedure is the same as in Example 3, 3-oxo-2,3-dihydrobenzothiophene being used as the starting material.

The following are obtained successively in the same manner:

(a) 2-Oxo-2,3-dihydro-9-thia-3,4-diazafluorene. M.p.=>260° C.

(b) 2-Chloro-9-thia-3,4-diazafluorene. M.p.=180° C.

(c) SR 44289 A.
Base: M.p.=138°–140° C.
Dihydrochloride: M.p.=236°–238° C.

The dihydrochloride crystallizes with 0.5 molecule of water.

EXAMPLE 8

5-Chloro-2-(2-diethylaminoethylamino)-9-oxa-3,4-diazafluorene fumarate (I) X=O; $R_1$=5-Cl; $R_2$=

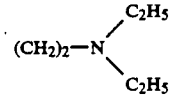

The procedure is the same as in Example 3, 4-chloro-3-oxo-2,3-dihydrobenzofuran being used as the starting material.

The following are prepared successively in the same manner:

(a) 5-Chloro-2-oxo-2,3-dihydro-9-oxa-3,4-diazafluorene. M.p.=>260° C.

(b) 2,5-Dichloro-9-oxa-3,4-diazafluorene.
M.p.=174°–176° C.

(c) SR 45148 A isolated in the form of the fumarate.
M.p.=232°–234° C. (ethanol).

The products according to the invention were studied for their therapeutic action. The interaction of the products according to the invention with muscarinic cholinergic receptors was determined in particular.

In mammals, there are two subclasses of muscarinic cholinergic receptors: the $M_1$ and $M_2$ receptors.

The $M_1$-type receptors are concentrated in certain areas of the brain, such as the hippocampus, the cerebral cortex and the striatum, and also in the sympathetic ganglia. These binding sites can be selectivity labeled with [$^3$H] pirenzepine ([$^3$H]PZ). The $M_2$-type receptors predominate in the heart and ileum and can be labeled with [$^3$H] N-methylscopolamine ([$^3$H]NMS). To determine the selectivity of the products of the invention towards the $M_1$ and $M_2$ sites, we studied their interaction in vitro with [$^3$H]PZ and [$^3$H]NMS bound with a high affinity to membranes of rat hippocampus and membranes of smooth muscle of guinea-pig ileum, respectively.

METHODOLOGIES (A) Test for Affinity for the $M_1$-Type Muscarinic Cholinergic Receptor The interaction of the molecules with $M_1$-type muscarinic receptors was studied by in vitro measurement, on a homogenate of rat hippocampus, of the displacement of tritiated pirenzepine ([$^3$H]PZ) from its specific binding sites. Aliquots (10 $\mu$l) of a 5% (w/v) homogenate of rat hippocampus in an $Na_2HPO_4$ buffer (50 mM, pH 7.40) are incubated for 2 h at 4° C. in the presence of [$^3$H]PZ (76 Ci/nmol; final concentration: 1 nM) and increasing concentrations of products to be studied. The final volume is 2 ml. The reaction is stopped by centrifugation for 10 min at 50,000×g. After decantation and washing of the residues, the bound radioactivity is counted by liquid scintillation. The non-specific binding is determined in the presence of 10 $\mu$mol/l of atropine sulfate. The 50% inhibitory concentration ($IC_{50}$) is determined graphically (Ref.: Watson J. D., Roeskoe W. R. and Yamamura H. I., Life Sci., 31, 2019–2029, 1982).

(B) Test for Affinity for the $M_2$-Type Muscarinic Cholinergic Receptor

The interaction with $M_2$-type muscarinic receptors was studied by in vitro measurement, on a homogenate of smooth muscle of guinea-pig ileum, of the displacement of tritiated N-methylscopolamine ([$^3$H]NMS) from its specific binding sites. Aliquots (50 $\mu$l) of a 0.625% (w/v) homogenate of smooth muscle of guinea-pig ileum in MEPES buffer (20 mM) containing NaCl (100 mM) and $MgCl_2$ (10 mM) (final pH: 7.5) are incubated for 20 min at 30° C. in the presence of [$^3$H]NMS (85 Ci/nmol; final concentration: 0.3 nM) and increasing concentrations of products to be tested. The final volume is 1 ml. The reaction is stopped by centrifugation for 5 min at 15,000×g. The non-specific binding is determined in the presence of 10 $\mu$mol/l of atropine sulfate. (Ref.: Hammer R., Berrie C. P., Birdsall N. I. M., Burgen A. S. V. and Hulme E. C., Nature, 283, 90–92, 1980; Hulme E. C., Birdsall N. I. M., Burgen A. S. V. and Mettha P., Mol. Pharmacol., 14, 737–750, 1978).

RESULTS

Table 2 indicates the affinities of the products of the invention for $M_1$ and $M_2$ receptors. The results are expressed as 50% inhibitory concentrations ($IC_{50}$), i.e. the concentration (in $\mu$M) which causes a 50% displacement of the tritiated ligand bound to the membrane receptors. The $IC_{50}$ for displacement of $^3$H-pirenzepine represents the affinity for the $M_1$ receptor; the $IC_{50}$ for displacement of $^3$H-NMS represents the affinity for the $M_2$ receptor.

The Table also indicates, in the 3rd column, the ratio r of the $M_1$ and $M_2$ $IC_{50}$ values, which expresses the selectivity of the products towards one of the receptor types.

TABLE 2

| Product no. | $^3$H-Pirenzepine ($M_1$) $IC_{50}$ $\mu$M | $^3$H-NMS ($M_2$) $IC_{50}$ $\mu$M | r = ($M_2/M_1$) |
|---|---|---|---|
| SR 44288 A | 3 | >100 | >33 |
| SR 44289 A | 3.5 | 100 | 28 |
| SR 45040 A | 0.7 | 45 | 64 |
| SR 45041 A | 0.1 | 10 | 100 |
| SR 45042 A | 0.1 | 50 | 500 |
| SR 96056 A | 0.15 | 3.6 | 24 |
| SR 96094 A | 3.6 | >100 | >27 |

These results show that the compounds according to the invention have a strong affinity for muscarinic cholinergic receptors with a marked specificity for $M_1$-type central receptors.

The compounds according to the invention were also subjected to a pharmacological study in vivo.

PHARMACOLOGICAL STUDY IN VIVO

Pirenzepine (PZ) is a specific antagonist of $M_1$ central muscarinic cholinergic receptors. The intrastriatal injection of PZ into mice induces rotational behavior. The antagonism of this behavior by the products according to the invention was studied.

The products according to the invention are injected intraperitoneally (i.p.) after solubilization in distilled water or suspension in a 5% solution of gum arabic. The control animals receive an injection of the pure solvent under the same conditions.

The animals used are female mice (Swiss, CD 1, Charles River, France) with a body weight of between 25 and 30 grams.

Pirenzepine is dissolved in a phosphate buffer; the pH of the solution is 6.

The products to be studied or their solvents are injected intraperitoneally, in a volume of 0.4 ml per 20 g of body weight, 15 minutes before a direct injection of pirenzepine at a dose of 1 $\mu$l of solvent into the right striatum of the mouse, according to the method described by P. WORMS et al. in Eur. J. Pharmacol., 1986, 121, 395–401.

The number of contralateral rotations (rotations in the opposite direction to the side injected) was counted for three 2-minute periods after the injection of pirenzepine: minutes 2 to 4, 8 to 10 and 13 to 15. Each treatment includes 1 to 3 doses and 10 animals per dose. For each treatment, the total number of rotations and the percentage antagonism compared with the control group are calculated.

The results are reported in Table 3.

TABLE 3

| Product no. | Pirenzepine antagonism at | | |
|---|---|---|---|
| | 3 mg/kg, i.p. | 10 mg/kg, i.p. | 30 mg/kg, i.p. |
| SR 44288 A | −32* | −52** | −100** |
| SR 44289 A | −42* | −85** | — |
| SR 45040 A | −47** | — | — |
| SR 45041 A | −72** | — | — |
| SR 45042 A | −52** | — | — |
| SR 96056 A | −14 | −55** | −79** |
| SR 96094 A | −8 | −20* | −85** |

*p <0.05
**p <0.01 vs control animals

Finally, the compounds according to the invention showed no signs of apparent toxicity at the doses at which they are active.

Consequently, the compounds (I) can be used as drugs, especially in cases where a cortical cholinergic deficit is evident and in particular in the case of dementia of the Alzheimer type.

According to another of its features, the present patent application therefore relates to pharmaceutical compositions in which at least one of the compounds of formula (I) or one of their salts is present as the active ingredient.

In the pharmaceutical compositions of the present invention for oral, sublingual, subcutaneous, intramuscular, intravenous, percutaneous or rectal administration, the active ingredients of formula I above can be administered to humans in unit forms of administration, mixed with conventional pharmaceutical excipients, especially for the treatment of senile dementia. Appropriate unit forms of administration include forms for oral administration, such as tablets, gelatin capsules, powders, granules and solutions or suspensions to be taken orally, forms for sublingual and buccal administration, forms for subcutaneous, intramuscular or intravenous administration and forms for rectal administration.

To obtain the desired effect, the dose of active principle can vary between 50 and 2000 mg per day.

Each unit dose can contain from 10 to 500 mg of active ingredient in combination with a pharmaceutical excipient. This unit dose can be administered 1 to 4 times per day.

If a solid composition is prepared in the form of tablets, the main active ingredient is mixed with a pharmaceutical vehicle such as gelatin, starch, lactose, magnesium stearate, talc, gum arabic or the like. The tablets can be coated with sucrose or other appropriate materials or they can be treated so that they have a prolonged or delayed activity and so that they release a predetermined amount of active principle continuously.

A preparation in the form of gelatin capsules is obtained by mixing the active ingredient with a diluent and pouring the resulting mixture into soft or hard gelatin capsules.

Powders or granules which are dispersible in water can contain the active ingredient mixed with dispersants or wetting agents or with suspending agents such as polyvinylpyrrolidone, as well as with sweeteners or taste correctors.

Rectal administration is effected using suppositories which are prepared with binders melting at the rectal temperature, for example cacao butter or polyethylene glycols.

Parenteral administration is effected using aqueous suspensions, isotonic saline solutions or injectable sterile solutions which contain pharmacologically compatible dispersants and/or wetting agents, for example propylene glycol or butylene glycol.

The active principle can also be formulated as microcapsules, if appropriate with one or more excipients or additives.

Thus, by way of example, it is possible to prepare gelatin capsules based on one of the compounds of Examples 1 to 8 and having the following composition:

| Active principle | 25 mg |
|---|---|
| Lactose | 110 mg |
| Magnesium stearate | 5 mg | by intimately mixing the above ingredients and pouring the mixture into hard gelatin capsules.

What is claimed is:

1. A tricyclic compound having the formula

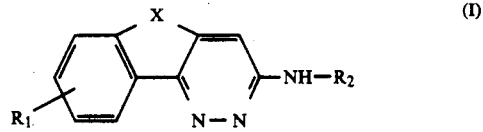

in which:

X represents an oxygen or sulfur atom or X represents —OCH$_2$— or —SCH$_2$—;

R$_1$ represents hydrogen or a halogen atom; and

R$_2$ represents:

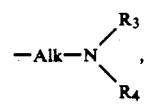

in which:

Alk represents a linear or branched alkylene group having from 2 to 5 carbon atoms, and R$_3$ and R$_4$ each independently represent hydrogen or a lower alkyl group having 1 to 4 carbon atoms; or R$_3$ and R$_4$, with the nitrogen atom to which they are bonded, form a pyrrolidin-1-yl, piperidino, morpholino or piperazin-1-yl group; or

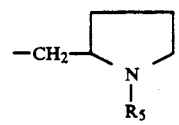

in which R$_5$ represents a lower alkyl group having 1 to 4 carbon atoms, or a salt thereof with a pharmaceutically acceptable mineral or organic acid.

2. A compound according to claim 1, wherein R$_1$ is a chlorine atom.

3. A pharmaceutical composition comprising an amount effective to treat cortical cholinergic deficiencies of at least one compound of formula (I), in combination with a pharmaceutically acceptable vehicle.

4. A pharmaceutical composition as claimed in claim 3, wherein the cortical cholingeric deficiency is Alzheimer-type dementia.

* * * * *